United States Patent [19]

Bolen et al.

[11] Patent Number: 5,215,898

[45] Date of Patent: Jun. 1, 1993

[54] CYTOTOXIC PROTEIN FROM THE YEAST PICHIA INOSITOVORA

[75] Inventors: Paul L. Bolen; G. Thomas Hayman, both of Peoria, Ill.

[73] Assignee: The United States of America as represented by the Secretary of Agriculture, Washington, D.C.

[21] Appl. No.: 733,512

[22] Filed: Jul. 22, 1991

[51] Int. Cl.⁵ .......................... C12P 1/02; C07K 13/00
[52] U.S. Cl. ..................................... 435/71.1; 530/371
[58] Field of Search ............... 530/350; 435/71.1, 69.1

[56] References Cited

U.S. PATENT DOCUMENTS 4,418,150 11/1983 Gunge ................................. 435/256

OTHER PUBLICATIONS

G. T. Hayman & P. L. Bolen, Linear DNA Plasmids of *Pichia inositovora* Are Associated with a Novel Killer Toxin Activity, Curr. Genet. 19:389-393 (1991).

G. T. Hayman & P. L. Bolen, Linear DNA Plasmids of *Pinchia inositovora* Are Associated with a Novel Killer Toxin Activity, 15th Int. Conf. on Yeast Genetics & Molecular Biology, The Netherlands, Abstr. S548 (1990).

J. M. Ligon et al., Physical and Biological Characterization of Linear DNA Plasmids of the Yeast *Pinchia inositovora*, Plasmid 21: 185-194 (1989).

*Primary Examiner*—Margaret Moskowitz
*Assistant Examiner*—Lisa Bennett
*Attorney, Agent, or Firm*—M. Howard Silverstein; Randall E. Deck; John D. Fado

[57] ABSTRACT

A novel cytotoxic protein is described possessing antifungal activity and which may be used for the treatment of fungal infections, or the prevention or control of fungal growth, as well as being potentially valuable as a biopesticide such as an insecticide, nematicide, or herbicide. The protein is produced by culture of *Pichia inositovora* strain NRRL Y-18709, and may be subsequently recovered from the culture medium and purified.

9 Claims, No Drawings

CYTOTOXIC PROTEIN FROM THE YEAST *PICHIA INOSITOVORA*

BACKGROUND OF THE INVENTION

1. Field of the Invention

Historically, fungal infections, and specifically yeast infections, have been difficult to treat due to a lack of specificity and potency of available antifungal compounds. Similarly, in the food and beverage fermentation industry, there exists a continuing need for antifungal agents such as cytotoxic proteins to insure culture purity. Cytotoxic proteins in general may also be toxic to other organisms and hence useful as biopesticides, such as insecticides, nematicides, and/or herbicides.

The invention relates to novel cytotoxic proteins produced by the yeast *Pichia inositovora*. The cytotoxic proteins possess antifungal activity and may be used for the treatment of fungal infections, or the prevention or control of fungal growth. The proteins are also potentially valuable as biopesticides.

2. Description of the Prior Art

Numerous filamentous fungi and yeasts have been discovered to contain linear double-stranded DNA plasmids [Meinhardt et al., Curr. Genet., 17:89–95 (1990), and Samac and Leong, Mol. Plant-Microbe Interac., 2:155–159 (1989)]. Among the yeasts that contain these elements are Saccharomyces kluyveri [Kitada and Hishinuma, Mol. Gen. Genet., 206:377–381 (1987)], *Kluyveromyces lactis* [Stark et al., Yeast, 6:1–29 (1990)], *Phaffia rhodozyma* [Wilber and Proffitt, Yeast Genetics and Molecular Biology Meeting, Jun. 16–21, 1987, Genetics Society of America, San Francisco, CA, Abstract 106], *Saccharomycopsis crataegensis* [Sheperd et al., Curr. Genet., 12:297–304 (1987)], and *Pichia inositovora* [Ligon et al., Plasmid, 21:185–194 (1989)].

Although most fungal linear plasmids are mitochondrial [Samac and Leong, ibid] in the yeasts *K. lactis, S. cratagensis,* and *P. inositovora*, these elements have been found to be located in the cytoplasm. Based on shared characteristics with other linear DNA plasmids, such as 5' ends protected by proteins and terminal inverted repeats, these cytoplasmic episomes have been included in a class of DNA molecules with the proposed name "invertrons" [Sakaguchi, Microbiol. Rev., 54:66–74 (1990)].

Functions have been ascribed to linear DNA plasmids of yeasts in the *K. lactis* system, consisting of two plasmids, pGKL1 and pGKL2, which are 8.1 and 13.4 kilobase pairs (kbp) in size, respectively. The smaller of the two plasmids, pGKL1, has been shown to encode both production of and immunity to a three subunit proteinaceous toxin active against a wide range of yeast species [Gunge et al., J. Bacteriol., 145:382–390 (1981)]. A function has not yet been discovered for the linear DNA plasmids of the yeasts *S. kluyveri* and *S. crataegensis*.

SUMMARY OF THE INVENTION

We have now discovered a novel cytotoxic protein possessing antifungal activity and which may be used for the treatment of fungal infections, or the prevention or control of fungal growth, as well as being potentially valuable as a biopesticide such as an insecticide, nematicide, or herbicide. The protein is produced by culture of *Pichia inositovora* strain NRRL Y-18709, and may be subsequently recovered from the culture medium and purified.

In accordance with this discovery, it is an object of the invention to provide a novel cytotoxic protein which possesses antifungal activity, and a method for its production.

It is also an object of the invention to provide a cytotoxic protein which may be used for the treatment of fungal infections, or for the prevention and control of fungal growth in commercial applications.

It is yet another object of the invention to provide a cytotoxic protein which may have utility as a biopesticide, such as an insecticide, nematicide, or herbicide.

Other objects and advantages of this invention will become readily apparent from the ensuing description.

DETAILED DESCRIPTION OF THE INVENTION

The preferred yeast for use herein is a strain of *Pichia inositovora* that has been deposited under the Budapest Treaty in the Agricultural Research Service Culture Collection (NRRL), 1815N. University St., Peoria, Ill., and has been been assigned Accession Number NRRL Y-18709. This strain contains three linear DNA plasmids, designated pPinl-1, pPinl-2 and pPinl-3, which are approximately 18, 13 and 10 kbp in size, respectively. For the purpose of the invention, any isolate of this yeast having all the identifying characteristics of NRRL Y-18709, including subcultures thereof, are effective. Also effective are mutants of this strain which have been cured of the pPinl-2 plasmid or which contain pPinl-2 mutations, but which still possess the pPinl-1 and pPinl-3 plasmids. As will be described hereinbelow, other microbial transformants that have been transformed with an expression vector which includes the structural gene(s) coding for a cytotoxic protein homologous with that produced by NRRL Y-18709 may also be used.

The yeast of this invention may be cultivated by any conventional means and under any convenient aerobic conditions that are effective to promote growth and toxin production. It is believed that optimal toxin production is concurrent with log phase growth. The determination of suitable media and conditions may be readily determined by the practitioner skilled in the art. Any number of well-known carbon sources for cell growth of *Pichia inositovora* may be used. Although glucose is preferred, it is anticipated that any of glucuronic acid, inositol, ethanol, and D-glycerol, as well as a variety of other sources described in Hayman and Bolen [Current Genetics, 19:389–393 (1991), the contents of which are incorporated by reference herein] may be used. Optimal toxin production has been achieved in culture media supplemented with amino acids. The yeast will grow over wide pH and temperature ranges, with the acceptable ranges for toxin production being about 2–8 and about 20°–32° C., respectively, with a pH of about 3–6 and a temperature of about 25°–29° C. being preferred.

Under such suitable conditions, the subject yeast will produce the cytotoxic protein of this invention which may be subsequently recovered from the culture medium. Upon completion of the fermentation, the cells may be separated from the culture medium using techniques conventional in the art, such as centrifugation or filtration. The cytotoxic protein remaining in the culture broth may then be concentrated and purified. Concentration of the proteins, while optional, is advantageous owing to the relatively low concentration of the cytotoxic protein secreted into the broth during fermentation. Ideally, the protein should be concentrated about 500 to 1000 fold or more in order to minimize subsequent purification costs. Suitable techniques for concentration include but are not limited to evaporation or ultrafiltration. Separation by ultrafiltration provides the added advantage of partially purifying the cytotoxic protein by using filters having a molecular weight cut-off effective to allow passage of lower molecular weight components while holding the subject protein in the retentate. Preferably such filters should have about a 100,000 nominal molecular weight pore size.

Following concentration, the cytotoxic protein may be purified using techniques conventional in the art. Suitable purification techniques may be readily determined by the practitioner skilled in the art, and include but are not limited to dialysis and/or chromatography. For example, dialysis may be conducted employing membranes having a molecular weight cut-off effective to allow passage of lower molecular weight components from the concentrated fermentation broth while retaining the protein therein. In the alternative, or preferably following dialysis, the toxin may be purified using column chromatography techniques that employ matrices allowing separation of the protein from the broth based upon size (e.g., HPLC size exclusion chromatography as described hereinbelow), charge (e.g., DEAE), or affinity (e.g., Cibacron blue F3GA dye linked matrices, Bio-Rad Laboratories, Richmond, CA). Affinity separation matrices are well known and include matrices having antibodies specific to the target protein, and other selective protein binding ligands [see "Data Sheet for MIMETIC Ligand A6XL Adsorbents," and brochure for "Protein Isolation Kit For Sorbent Identification PIKSI", Affinity Chromatography Ltd, Freeport, Ballasalla, Isle of Man, British Isles; "Chromatographic Supports," In: Life Science Research Products Price List Q, (March 1991), pages 25-32, Bio-Rad Laboratories, Richmond, CA, the contents of which are incorporated by reference herein]. Following adsorption, the protein may be recovered from the chromatography matrix by elution in pure or substantially pure form.

The cytotoxic protein of this invention exhibits all the identifying characteristics of a protein produced in accordance with the process described herein. The subject protein has a molecular weight greater than 100 kilodaltons (kD). Using size exclusion chromatography, the molecular weight has been determined to be approximately 160 kD as determined by the peak toxin activity of time collected aliquots when compared to the elution times of known standards. Surprisingly, the protein has been found to be toxic to a relatively narrow range of yeasts. Although the complete range has not been determined, the protein is characterized by its cytotoxic activity to the yeast indicator strains: *Saccharomyces cerevisiae* strain GS-1688 and genetically similar strain GS-1731, *Cephaloascus albidus* strain NRRL Y-18710, and *Citeromyces matritensis* strain NRRL Y-18711. However, the protein was not toxic to other indicator strains tested, including *Saccharomyces cerevisiae* strains GS-1725 and GS-643. Strains NRRL Y-18710 and Y-18711 have been deposited under the Budapest Treaty in the Agricultural Research Service Culture Collection. The protein is also characterized by an optimal cytotoxic activity at a pH of between 3.4 and 4.2, when tested against *S. cerevisiae* strain GS-1688, in YEPD assay plates containing 50 mM citrate buffer. In addition, there is strong correlative evidence that the genes coding for the subject protein are on the above-mentioned pPinl-1 and pPinl-3 plasmids.

While the cytotoxin of this invention has been referred to as a single cytotoxic protein, it is understood that this toxin may be comprised of a single polypeptide, or two or more subunits linked together, for example, by disulfide or ionic bonds. Upon SDS-PAGE electrophoresis, three peptides having a molecular weight of about 110, 105 and 28 kD were identified in the concentrated culture supernatant of *P. inositovora* strain NRRL Y-18709, which were not present in the concentrated culture supernatant in strains of this yeast cured of the three linear DNA plasmids (pPinl-1, pPinl-2 and pPinl-3). At least one of these peptides is likely a component of the subject protein. However, due to the rigorous conditions incurred during SDS-PAGE analysis and probable protein dissociation, the exact nature of the relationship between these peptides has not been determined, and it is not known if any of the identified peptides are degradation products of the others.

As referred to hereinabove, production of the protein by the use of recombinant DNA techniques, for the purpose of this invention, should be understood to include the suitable employment of structural genes coding for the protein. The protein may also be obtained by transforming a microorganism, such as a bacterium, yeast, or fungus, using an expression vector including a promoter or operator, or both, operably linked together with the structural genes, and causing such transformed microorganisms to express the protein. Further, as noted above, there is strong correlative evidence that the genes coding for the subject protein are on the pPinl-1 and/or pPinl-3 plasmids. It is anticipated that microorganisms and especially yeast transformed with these plasmids may be utilized for production of the protein. For example, suitable techniques include those described by Gunge [U.S. Pat. No. 4,418,150, issued Nov. 29, 1983], the contents of which are incorporated by reference herein.

In use, it is envisioned that the recovered, and preferably purified, cytotoxic protein will be formulated in conjunction with a suitable inert carrier or vehicle as known in the art. The skilled practitioner will recognize that such carriers should of course be compatible with the protein, and should be pharmaceutically acceptable when employed for medicinal purposes. When employed as a biopesticide, the pesticidal agent may be prepared directly from culture extracts, thereby obviating the need to isolate the compound in pure form.

The concentration and amount of the protein in the final composition may vary depending upon the target organism, environment and mode of application, type of response needed, and period or duration of treatment. In any event, the cytotoxic protein should be employed in an amount effective to induce the preferred response as determined by routine testing. Where the desired response is antifungal activity, the effective amount is defined to mean that quantity which will result in significant prevention of fungal growth of the target fungus, as compared to an untreated fungus.

The following examples are intended only to further illustrate the invention and are not intended to limit the scope of the invention which is defined by the claims.

EXAMPLE 1

Culture of Yeast. Unless otherwise specified, all yeasts were grown using YEPD (1% yeast extract, 2.0% Bacto-peptone, and 2.0% glucose). For assays, this YEDP medium was buffered with 50 mM sodium citrate buffer at the appropriate pH. Solid media contained 1.5% agar. All cultures were normally grown at 25° C. unless otherwise stated.

EXAMPLE 2

Isolation of Cured Strains. Cultures from single colony isolates of *Pichia inositovora* strain NRRL Y-18709 were cured of their linear DNA plasmids by growing sequential 3- to 4-day YEPD cultures containing 50 μg/ml bisbenzimide with several transfers at 25° C. and 29° C., and by exposure to UV light (UV; 254 nm) at a level sufficient to kill approximately 80% of the cells, essentially as described by Worsham and Goldman [Mol. Gen. Genet., 214:348–352 (1988)]. Colonies from the treated cultures were analyzed for linear plasmids. Plasmids were isolated from 25 ml cultures, subjected to 0.8% agarose gel electrophoresis and stained with ethidium bromide using previously described procedures [Ligon et al., Plasmid, 21:185–194 (1989)]. Of 148 colonies analyzed from bisbenzimide-treated cultures, five were found to contain no detectable plasmid DNA. Five others lacked pPin-2, and one harbored pPinl-1, pPinl-3 and what appeared to be pPinl-2 with a deletion. See Example 6, hereinbelow. The remaining strains contained all three linear plasmids. Of 28 isolates from a UV-treated culture, only three retained detectable plasmid DNA. These three strains harbored pPinl-1 and pPinl-3, and appeared to contain pPinl-2 at lower levels than the wild-type strain. Plasmid preparations from the wild-type and cured strains isolated in the absence of RNase showed no distinguishable RNA plasmid species.

EXAMPLE 3

Toxin Bioassays. Killer toxin activity present in culture supernatants of both *P. inositovora* wild-type (NRRL Y-18709) and cured strains were assayed using a modification of the method of Worsham and Bolen [ibid.]. Cells were harvested from 1 or 2 l YEPD cultures by centrifugation at 3,000 g for 10 min. Culture supernatants were concentrated 500 to 1,000 fold using Amicon 52 and 8400 ultrafiltration units fitted with YM100 filters (100,000 MW cut-off), operated under 20 psi $N_2$ at room temperature. Concentrated supernatants were filter sterilized and stored at 4° C. Aliquots of these culture concentrates (5 μl) were applied to the wells of a 24-well plastic microtiter dish, each well containing 1 ml citrate-buffered YEPD agar, and allowed to dry. Molten top agar (0.5 ml; YEPD plus 0.7% agar) held at 50° C. was inoculated with 30 μl of an overnight culture of an indicator strain which had been diluted to an $A_{600}$ of approximately 0.7. Indicator strains used in the overlays were: (1) *P. inositovora* wild-type strain NRRL Y-18709; (2) *P. inositovora* GS-931 (a pPinl-2 deletion mutant from Example 2); (3) *P. inositovora* GS-929 (a strain cured of pPinl-2 from Example 2); (4) *P. inositovora* GS-1004 (a strain cured of all linear plasmids from Example 2); (5) *Saccharomyces cerevisiae* strain GS-1688; (6) *Citeromyces matritensis* NRRL Y-18711; (7) *Cephaloascus albidus* NRRL Y-18710; and (8) *Saccharomyces cerevisiae* strain GS-1731.

The top agar was then mixed and overlaid on the agar in each test well.

The wild-type strain, three bisbenzimide-cured and 16 UV cured

P. inositovora isolates were all found to be insensitive to culture supernatants of both the wild-type strain and a cured isolate. However, the two genetically similar strains of *S. cerevisiae*, GS-1688 and GS-1731, were discovered to be very sensitive to wild-type culture supernatants but insensitive to sterile culture concentrates of the cured strain. The two other yeast species, *Citeromyces matritensis* NRRL Y-18711 and *Cephaloascus albidus* NRRL Y-18710, were also found to be sensitive to culture supernatants of the wild-type but not the cured strain.

The exhibition of toxin activity in the culture supernatant of the wild-type strain NRRL Y-18709, but not in that of the cured strains, indicates that toxin production is plasmid related, and that toxic activity is not the result of other concentrated culture medium components.

Production of toxin by *P. inositovora* isolates was assessed by the plate bioassay. Strains to be tested for toxin production were patched onto a YEPD-citrate pH 3.6 plate and grown for 2–3 days, and included: (1) *P. inositovora* wild-type strain NRRL Y-18709; (2) *P. inositovora* GS-931 (a pPinl-2 deletion mutant from Example 2); (3) *P. inositovora* GS-929 (a strain cured of pPinl-2 from Example 2); (4) *P. inositovora* GS-1004 (a strain cured of all linear plasmids from Example 2). The grown patches of cells were then killed by exposure to chloroform vapor for 10 min, followed by airing for 5 min. The plate was then overlaid with top agar seeded with *S. cerevisiae* strain GS-1688 and incubated for 24 to 48 hr. at 25° C. Following incubation, clear zones were found around the patches of growth for all strains except the fully cured strain, GS-1004. The 28 UV-treated *P. inositovora* isolates analyzed for plasmid content from Example 2 were also screened for toxin production in the plate bioassay. The only three strains that tested positive were the same three found to contain both pPinl-1 and pPinl-3. The data indicates that the pPinl-2 plasmid does not appear to be required for the expression of the toxin system of *P. insoitovora*, as its loss has no effect on toxin production or toxin sensitivity. On the other hand, toxin production is associated with the pPinl-1 and pPinl-3 plasmids of this yeast.

EXAMPLE 4

Toxin Characterization. To determine the optimum pH for toxin activity, the microtiter dish assay was used as in Example 3, with concentrated culture supernatant aliquots from strain NRRL Y-18709 being spotted on the agar in all wells, and using *S. cerevisiae* strain GS-1688 as the indicator. The pH of the citrate added to the agar in each well was varied by increments of 0.2, from pH 3.0 to 6.0. The data indicated that toxin activity was strongest when citrate buffers of pH 3.4 to 4.2 were used.

Exposure of the toxin in the culture concentrates to 65° C. for 10 min resulted in complete loss of activity against strain GS 1688. Incubation of toxin in proteinase K buffer [Sambrook et al., Molecular Cloning: a Laboratory Manual, Cold Spring Harbor Laboratory, Cold Springs Harbor, N.Y., (1989)], lacking sodium dodecyl sulfate and containing 1 mg/ml proteinase K, at 37° C. for 2 hr significantly reduced activity, compared to incubation of the toxin in the presence of proteinase K buffer alone, which had no effect.

EXAMPLE 5

Toxin Purification and molecular weight. Cells of *P. inositovora* strain NRRL Y-18709 were grown in 10 flasks, each containing 1.5 l of YEPD medium (1.5 ml of inoculum/1.5 l), and grown overnight at 25°–29° C. with shaking. The cells were separated from the supernatant by centrifugation in a Sorvall GS-3 rotor spinning at 7,000 rpm for 10–15 min, and the pooled supernatants ultrafiltered through a 100,000 NMWL filter (#PTHK 000 05, Millipore Corporation, Bedford, MA) using a Pellicon Cassette Ultrafiltration System (Millipore Corporation) to obtain a 300–500 ml retentate volume. This retentate was then again centrifuged 15 min in the same manner as above to remove larger particles and cells. The supernatant was then ultrafiltered through a 100,000 NMWL filter (#PTHK OMP04, Millipore Corporation) using a Minitan Ultrafiltration System (Millipore Corporation) to obtain a 30–50 ml retentate volume comprising concentrated cytotoxic protein. This retentate was next placed in Spectrapor Dialysis Tubing having a 12,000–14,000 molecular weight cut-off (#08-667E, Fisher Scientific Co., Pittsburgh, PA) and dialyzed overnight against 3 l distilled water. The dialysate was then ultrafiltered through a YM100 membrane filter (100,000 MW cut-off) in a Model 52 Stirred Cell Ultrafiltration System (Amicon Division, W. R. Grace & Co., Danvers, MA) to obtain a 1–1.5 ml retentate. Finally, the retentate was sterile filtered through a 0.22 μM Millex-GV (#SLGV 0130S) filter (Millipore Corporation) and stored until use. This concentrated and sterile filtered product comprised substantially pure cytotoxic protein.

Molecular weight determination and further purification of the cytotoxic protein was conducted by HPLC protein separation with a size exclusion chromatography column [Bio-Sil SEC-400, 300 mm×7.5 mm (Bio-Rad, Richmond, CA)] of 100 μl purified sample obtained as above. According to the process, 100 mM potassium phosphate buffer at pH 7.0, was used, and with a flow rate of 1 ml per min. Detection was at 280 nm, and the standards used were SEC Protein Standards of 670 kD–1.35 kD (Bio-Rad). The size of the cytotoxic protein was approximately 160±50 kD as determined by peak toxin activity of the time collected aliquots when compared to the elution times of the standards.

EXAMPLE 6

Electrolution and Southern Hybridization. Electrolution and radiolabeling of DNA probes, and hybridization analyses, were carried out as described by Ligon et al. (ibid.). To determine whether pPinl-2 had suffered a deletion in *P. inositovora* strain GS-931 and had been cured in strain 929, hybridizations of a blot made from a gel identical to Example 2 were performed using electroluted, $^{32}P$-labeled pPinl-2 DNA as a probe. pPinl-2 of wild-type strain NRRL Y-18709 and the putative pPinl-2 deletion plasmid of strain GS-931 hybridized strongly to the probe, indicating that the latter plasmid is in fact a deletion derivative of pPin-2. No hybridization signal was detected between the positions of pPinl-1 and pPinl-3 of strain GS-929, indicating that this isolate is completely cured of pPinl-2.

It is understood that the foregoing detailed description is given merely by way of illustration and that modifications and variations may be made therein without departing from the spirit and scope of the invention.

We claim:

1. An isolated protein produced by *Pichia inositovora* strain NRRL-18709 having a molecular weight of about 160 kD as determined by size exclusion chromatography, said protein being characterized by the property of being cytotoxic against *Cephaloascus albidus* strain NRRL Y-18710, and *Citeromyces matritensis* strain NRRL Y-18711, and wherein said protein is free of cells of said *Pichia inositovora*.

2. A composition comprising the isolated protein of claim 1 and an inert carrier.

3. A method for producing a cytotoxic protein comprising:
   (a) providing cells selected from the group consisting of:
      (1) *Pichia inositovora* strain Y-18709 containing three linear DNA plasmids of approximately 18, 13 and 10 kbp and which produces a protein having a molecular weight of about 160 kD as determined by size exclusion chromatography, and said protein being characterized by the property of being cytotoxic against *Cephaloascus albidus* strain NRRL Y-18710, and *Citeromyces matritensis* strain NRRL Y-18711; and
      (2) mutants of said *Pichia inositovora* strain Y-18709 which lack said approximately 13 kbp DNA linear plasmid or include mutations in said approximately 13 kbp DNA linear plasmid and which produce said protein;
   (b) culturing said cells in a culture medium and under conditions effective to produce said protein; and
   (c) separating said protein from said cells in said culture medium.

4. A method as described in claim 3 further comprising the step of isolating said protein from said culture medium obtained from said step (b).

5. A method as described in claim 3 further comprising the steps of concentrating and subsequently isolating said protein from said culture medium obtained from said step (b).

6. A cytotoxic protein produced by the process comprising:
   (a) culturing cells of *Pichia inositovora* strain NRRL 18709 in a culture medium and under conditions effective to produce a cytotoxic protein having a molecular weight of about 160 kD as determined by size exclusion chromatography, said protein being characterized by the property of being cytotoxic against *Cephaloascus albidus* strain NRRL Y-18710, and *Citeromyces matritensis* strain NRRL Y-18711; and
   (b) separating said cells from said protein in said culture medium.

7. The protein as described in claim 6, wherein said process further comprises separating components having a molecular weight less than about 100 kD, from said culture medium containing said protein of step (b).

8. A composition comprising the protein of claim 6 and an inert carrier.

9. A composition comprising the protein of claim 7 and an inert carrier.